US010105127B2

(12) United States Patent
Abri et al.

(10) Patent No.: US 10,105,127 B2
(45) Date of Patent: Oct. 23, 2018

(54) SURGICAL INSTRUMENT WITH A MANUAL CONTROL

(71) Applicant: Karl Storz SE & Co. KG, Tuttlingen (DE)

(72) Inventors: Omid Abri, Berlin (DE); Stephan Schrader, Berlin (DE); Jonas Forster, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 485 days.

(21) Appl. No.: 14/923,006

(22) Filed: Oct. 26, 2015

(65) Prior Publication Data

US 2016/0113637 A1 Apr. 28, 2016

(30) Foreign Application Priority Data

Oct. 27, 2014 (DE) .................. 10 2014 115 600

(51) Int. Cl.
*A61B 17/00* (2006.01)
*A61B 17/29* (2006.01)
(Continued)

(52) U.S. Cl.
CPC .... *A61B 17/00234* (2013.01); *A61B 17/2909* (2013.01); *A61B 19/22* (2013.01); *A61B 34/70* (2016.02); *A61B 34/74* (2016.02); *A61B 34/76* (2016.02); *A61B 19/2203* (2013.01); *A61B 2017/0046* (2013.01); *A61B 2017/00398* (2013.01); *A61B 2017/00424* (2013.01); *A61B 2017/00477* (2013.01); *A61B 2017/2919* (2013.01); *A61B 2019/2269* (2013.01)

(58) Field of Classification Search
None
See application file for complete search history.

(56) References Cited

U.S. PATENT DOCUMENTS 5,976,121 A 11/1999 Matern et al.
6,299,624 B1 10/2001 Cuschieri et al.
(Continued)

FOREIGN PATENT DOCUMENTS

DE 69430751 T2 3/2003
EP 0781112 B1 12/1998
(Continued)

OTHER PUBLICATIONS

German Search Report Application No. 10 2014 115 600.5 dated Aug. 7, 2015 10 pages.
(Continued)

*Primary Examiner* — Ankit D Tejani
(74) *Attorney, Agent, or Firm* — Whitmyer IP Group LLC

(57) ABSTRACT

Surgical instrument with a manual control device for actuation with a hand, wherein the control device can be displaced between a closed position and an opened position and the control device has: a finger lever with a first point of articulation and a second point of articulation, a central element with a third point of articulation and a fourth point of articulation, a connecting lever, which is pivotably arranged at the first point of articulation and at the third point of articulation, and a thumb lever, which is pivotably arranged at the second point of articulation and at the fourth point of articulation.

18 Claims, 10 Drawing Sheets

(51) Int. Cl.
*A61B 19/00* (2006.01)
*A61B 34/00* (2016.01)

(56) References Cited

U.S. PATENT DOCUMENTS

| 2007/0005002 A1 | 1/2007 | Millman et al. |
| 2008/0154246 A1 | 6/2008 | Nowlin et al. |
| 2008/0262538 A1* | 10/2008 | Danitz ................ A61B 1/0053 606/205 |
| 2013/0331826 A1 | 12/2013 | Steege |

FOREIGN PATENT DOCUMENTS

| GB | 2302655 A | 1/1997 |
| WO | 9918863 A1 | 4/1999 |
| WO | 2012127404 A2 | 9/2012 |
| WO | 2013018912 A1 | 2/2013 |

OTHER PUBLICATIONS

European Search Report Application No. EP15190736.7 completed: Mar. 4, 2016; dated Mar. 16, 2016 10 pages.

* cited by examiner

SURGICAL INSTRUMENT WITH A MANUAL CONTROL

CROSS REFERENCES TO RELATED APPLICATIONS

This application claims priority from German patent application 10 2014 115 600.5, filed on Oct. 27, 2014. The entire contents of these priority applications are incorporated herein by reference.

BACKGROUND OF THE INVENTION

The present disclosure relates to a surgical instrument with a manual control device for actuation by hand, wherein the control device can be displaced between a closed position and an opened position. The displacement takes place by a manual action being imparted to the control device by the hand of a user, in that the latter opens and closes the hand.

There are many tools and instruments that a user actuates manually with his or her hand. Some of these instruments require special ergonomics for the actuation, for example because the actuation of the instrument must be possible with a fine touch, because frequently repeated actuation of the instrument is required or because certain actuating positions of the instrument have to be constantly maintained over a relatively long time.

These instruments also include surgical instruments, in particular minimally invasive surgical instruments. These have at least one grip at the proximal end, which allows a user, in particular a surgeon or an assistant, to hold and actuate the instrument. Such instruments have to be ergonomically suitable for gripping and ergonomically suitable for actuating, and must also be so for hands of any size. Finally, it must also be possible for the user to be able to exert a sufficient force on the control device repeatedly in a convenient way and in various positions of the control device.

Many of the grips for such instruments are substantially pistol-like. This form of grip can be gripped well in a wide range of angles, also allowing work to be carried out well in different positions and with unfavorable holding angles. These grips often have finger loops, with which work can be carried out with a sufficiently fine touch.

In this connection, reference may be made merely by way of example to the control devices that are shown in U.S. Pat. No. 6,299,624 B1, US 2007/0005002 A1 and US 2008/0154246 A1. Reference should also be made to U.S. Pat. No. 5,976,121, where a particularly ergonomic control device is shown.

In spite of the large number of manual control devices, there is also still a need for control devices that make convenient and intuitive operation possible for the user even over a relatively long period of time.

SUMMARY OF THE INVENTION

It is an object of the present disclosure to provide an improved surgical instrument with a manual control device for actuation by hand that makes convenient and ergonomic actuation possible, in particular by opening and closing the hand.

According to a first aspect, there is provided a surgical instrument with a manual control device for actuation with a hand, wherein the control device can be displaced between a closed position and an opened position and the control device has:
- a finger lever with a first point of articulation and a second point of articulation, wherein the finger lever has a finger resting portion, which is formed as a continuation from the first point of articulation as a first extent of the finger lever between the second point of articulation and the first point of articulation,
- a central element with a third point of articulation and a fourth point of articulation,
- a connecting lever, which is pivotably arranged at the first point of articulation and at the third point of articulation, so that the connecting lever is pivotable in relation to the central element and in relation to the finger lever and that the first point of articulation is displaceable in a guided manner along a first curved path around the third point of articulation,
- a thumb lever, which is pivotably arranged at the second point of articulation and at the fourth point of articulation, so that the thumb lever is pivotable in relation to the central element and in relation to the finger lever and that the second point of articulation is displaceable in a guided manner along a second curved path around the fourth point of articulation.

Within the context of the improvement to be achieved, it has been found that a problem with known manual control devices is that they do not sufficiently make allowance for the actual movement of the hand of a user during the opening and closing of the hand. This has the effect that known manual control devices may appear to be ergonomically and conveniently operable when the proposed technique is considered, but in practice are not found to be so by the user, especially in the case of lengthy procedures.

It has also been found in this connection that at least part of the problem appears to be that the thumb and fingers of a hand do not move precisely on a circular path during opening as in the case of a hinge. Rather, it has been found that, during opening of the hand, the thumb and fingers initially move away from one another almost in a straight line. The thumb then pivots quite quickly onto a curved path, in particular a circular path, while the fingers continue to advance on an at least approximately straight path. Only once the process of opening the hand is already well advanced do the fingers also turn onto a curved path, in particular onto a circular path.

For the manual control device disclosed here, allowance has also been made for the fact that it is also intended to be possible to provide such a control device at low cost. It has been desired to find a solution that better replicates the natural opening movement of the hand and nevertheless has a mechanical construction that is as simple as possible. A mechanically simple construction may contribute to the reliability of the control device and to low-cost production of the control device.

One feature of the disclosed manual control device is that, although the various levers, that is to say the finger lever, the connecting lever and the thumb lever, pivot about points of articulation, that is to say actually move on a circular path, at the same time at least one of the points of articulation, in particular precisely two or at least two of the points of articulation, are displaced, so that, at least during a phase of the opening process, the distal end of the finger lever is displaced along an at least approximately linear path.

In a refinement of the disclosed subject-matter, the movement of at least one of the levers mentioned is mechanically or electrically detected and used for actuating, in particular for opening and closing, the surgical instrument. In a refinement of the disclosed subject-matter, when viewed along the longitudinal direction, the first point of articulation and the second point of articulation move in the direction of the distal side during the opening of the control device and move in the direction of the proximal side during the closing. In a refinement of the disclosed subject-matter, the finger resting portion has a width perpendicularly to the longitudinal direction, and, for an exemplary embodiment, also perpendicularly to the vertical direction, of at least 5 mm, or at least 10 mm, or of at least 20 mm, or of at least 30 mm.

For simplified orientation, here and hereinafter the terms distal and proximal are to be used as follows. The part of the control device that is closest to the midpoint of a hand of the user when the latter has placed his or her hand onto or into the control device is to be understood as proximal. The distal side of the control device is opposite from the proximal side in the longitudinal extent of the control device. This is where the fingertips of the user are located when he or she has placed his or her hand onto or into the control device. The longitudinal direction from proximal to distal may be understood for an exemplary embodiment, as a straight line that leads through the second and third points of articulation when the control device is closed. These orientation aids serve merely for a better understanding.

As still to be described later on the basis of exemplary embodiments, a first distal end of the finger lever is displaced during a phase of the opening process, in particular the beginning of the opening process, in such a way that the position of the first distal end remains at least substantially unchanged with respect to the longitudinal direction. This is achieved inter alia by providing that, while the finger lever pivots about the first point of articulation, the first point of articulation is at the same time displaced in the direction of the distal side. Thus, the turning movement of the finger lever around the first point of articulation, which would actually bring about a displacement of the first distal end in the direction of the proximal side, is at least partially compensated or overcompensated by the displacement of the first point of articulation in the direction of the distal side.

In order to understand the compensation or overcompensation better, it shall be assumed hereinafter that during opening the first distal end of the finger lever is displaced by a distance x along the longitudinal direction and by a distance y along a vertical direction, which is perpendicular to the longitudinal direction. In a refinement of the disclosed subject-matter, the compensation or overcompensation is chosen such that the distance x, either in the direction of the distal side or in the direction of the proximal side, during an opening of the control device by 45° from the closed position is at most 0.25y, or 0.2y, or 0.15y, or 0.1y. In addition or alternatively, the compensation or overcompensation is chosen such that the distance x, either in the direction of the distal side or in the direction of the proximal side, during an opening of the control device by 30° from the closed position is at most 0.2y, or 0.15y, or 0.1y, or 0.05y.

In a refinement of the disclosed subject-matter, the control device is formed in such a way that the central element is stationary in relation to a midpoint of the hand during an opening and closing of the control device. This means that, although the levers mentioned are displaced, the control device as a whole is stationary with respect to the midpoint of the hand. If the central element is coupled to a surgical instrument, it may be achieved in this way that the midpoint of the hand is stationary in relation to the surgical instrument during an opening and closing of the control device. In other words, an opening and closing of the control device does not bring about a displacement of the central element or the surgical instrument in the longitudinal direction.

In a refinement of the disclosed subject-matter, a length of the finger resting portion is between 35% and 95% of the length of the finger lever, or between 45% and 90%, or between 55% and 85%, or between 65% and 80%. The length of the finger resting portion is to be understood here as meaning the distance from the first point of articulation to the distal end of the finger lever. The length of the finger lever is to be understood as meaning the distance from the second point of articulation via the first point of articulation to the distal end of the finger lever.

In a refinement of the disclosed subject-matter, the pivot axes, that is to say the axes about which the levers pivot at the points of articulation in relation to one another or in relation to the central element, run substantially parallel to one another. In addition or alternatively, the pivot axes run transversely in relation to a hand resting on the control device. The pivot axes may also be understood as parallel to a width direction, which is perpendicular both to the longitudinal direction and to the vertical direction.

In a refinement, the first curved path and/or the second curved path may be a circular path.

In a refinement of the disclosed subject-matter, the thumb lever has a thumb resting portion, which is formed as a continuation from the fourth point of articulation as a second extent of the thumb lever between the second point of articulation and the fourth point of articulation.

For this refinement, the thumb of the hand is also included in the movement during the opening and closing of the control device. This may allow a natural actuation by hand. In a refinement of the disclosed subject-matter, a length of the thumb resting portion is between 35% and 95% of the length of the thumb lever, or between 45% and 85%, or between 55% and 75%, or between 60% and 70%. The length of the thumb resting portion is to be understood here as meaning the distance from the fourth point of articulation to the distal end of the thumb lever. The length of the thumb lever is to be understood as meaning the distance from the second point of articulation via the fourth point of articulation to the distal end of the thumb lever.

In a refinement of the disclosed subject-matter, the connecting lever has an actuating portion, which is formed as a continuation from the third point of articulation as a third extent of the connecting lever between the first point of articulation and the third point of articulation.

For this refinement, a force that acts on the control device during the opening and closing of the hand may be converted easily into a pushing movement. In this case, both a positive push and a negative push, which is also referred to as a pull, can be produced.

In a refinement of the disclosed subject-matter, the central element has a fifth point of articulation and the control device has a first control element, which has a sixth point of articulation, is pivotably arranged at the fifth point of articulation and at the sixth point of articulation and is coupled to the connecting lever, so that the first control element is pivotable in relation to the central element and that the sixth point of articulation is displaceable in a guided manner along a third curved path around the fifth point of articulation.

This refinement may allow good transmission of a force acting on the control device as a result of the manual actuation. Since the fifth point of articulation is fixed in relation to the central element, a fixed part of an instrument may be arranged here. Since the sixth point of articulation is displaced when there is an actuation of the control device, a movable element of the instrument may be coupled here. When there is an actuation of the control device, the control device as a whole remains immovable in relation to the fixed part of the instrument; the actuation of the finger lever and possibly of the thumb lever however produces a movement of the sixth point of articulation and thereby a displacement of the movable part of the instrument.

In a refinement of the disclosed subject-matter, the central element has a seventh point of articulation and the control device has a second control element, which has an eighth point of articulation, is pivotably arranged at the seventh point of articulation and at the eighth point of articulation and is coupled to the connecting lever, so that the second control element is pivotable in relation to the central element and that the eighth point of articulation is displaceable in a guided manner along a fourth curved path around the seventh point of articulation.

This refinement may allow good transmission of a force acting on the control device as a result of the manual actuation. Since the seventh point of articulation is fixed in relation to the central element, a fixed part of an instrument may be arranged here. Since the eighth point of articulation is displaced when there is an actuation of the control device, a movable element of the instrument may be coupled here. When there is an actuation of the control device, the control device as a whole remains immovable in relation to the fixed part of the instrument; the actuation of the finger lever and possibly of the thumb lever however produces a movement of the eighth point of articulation and thereby a displacement of the movable part of the instrument.

The fifth point of articulation and the seventh point of articulation may be spaced apart from one another, for an exemplary embodiment, along a vertical direction, which is perpendicular to the longitudinal direction. In a refinement of the disclosed subject-matter, the fifth point of articulation and the seventh point of articulation coincide. Then, the first control element and the second control element are articulated at a common point of articulation.

In a refinement of the disclosed subject-matter, the connecting lever and the first control element are coupled by a first articulated connection, for an exemplary embodiment, by a first intermediate lever.

This refinement may allow an improved displacement of the first control element.

In a refinement of the disclosed subject-matter, the connecting lever and the second control element are coupled by a second articulated connection, for an exemplary embodiment, by a second intermediate lever.

This refinement may allow an improved displacement of the second control element.

In a refinement of the disclosed subject-matter, the first point of articulation is spaced apart from the second point of articulation by a first distance, the third point of articulation is spaced apart from the fourth point of articulation by a second distance and the first distance is between 25% and 125% of the second distance, o between 35% and 100%, or between 45% and 75%, or between 50% and 60%.

These relative distances have been found to be suitable in practical tests.

In a refinement of the disclosed subject-matter, the first point of articulation is spaced apart from the third point of articulation by a third distance, the second point of articulation is spaced apart from the fourth point of articulation by a fourth distance and the fourth distance is between 35% and 150% of the third distance, between 45% and 125%, or between 55% and 100%, or between 65% and 85%.

These relative distances have been found to be suitable in practical tests.

In a refinement of the disclosed subject-matter, the first point of articulation is spaced apart from the second point of articulation by a first distance, the second point of articulation is spaced apart from the fourth point of articulation by a fourth distance and the first distance is between 40% and 150% of the third distance, or between 45% and 125%, or between 50% and 100%, or between 60% and 80%.

These relative distances have been found to be suitable in practical tests.

In a refinement of the disclosed subject-matter, the control device also has a push rod, which is coupled in an articulated manner to at least one element selected from the group comprising the finger lever, the thumb lever and the connecting lever.

This design makes it possible in an easy way to convert the movement during the opening and closing of the control device into an at least approximately linear pushing movement. Here, too, the push may in this case be both positive and negative. For an exemplary embodiment, the push rod is coupled in an articulated manner to the thumb lever, in this case in particular to a portion of the thumb lever that lies between the second point of articulation and the fourth point of articulation.

In a refinement of the disclosed subject-matter, the control device is formed in such a way that a fifth distance between the second point of articulation and the third point of articulation is reduced during an opening of the control device.

This refinement may allow the previously described compensation or overcompensation in an easy way when the displacement of the finger lever or the first distal end of the finger lever occurs. In the same way, the fifth distance is increased during the closing of the control device.

In a refinement of the disclosed subject-matter, the central element has a palm rest and/or an adapter for a coupling to a surgical instrument or to a haptic input device.

For this refinement, the control device may be coupled easily to an instrument. Moreover, the additional or alternative palm rest may allow comfortable and relaxed gripping of the control device. In a refinement of the disclosed subject-matter, the manual control device is coupled to a surgical instrument from the CLICKline range of the Karl Storz company.

In a refinement of the disclosed subject-matter, the control device also has a motor, which interacts with at least one element selected from the group comprising the finger lever, the thumb lever and the connecting lever, in order to provide haptic feedback and/or motorized assistance when opening and/or closing the control device.

This design may allow telemanipulation or working in a virtual test environment. As an alternative or in addition, the user can be assisted when opening and/or closing the control device or when maintaining a constant position.

In a refinement of the disclosed subject-matter, the control device also has a measuring device, which is designed for determining a degree of opening of the control device, for an exemplary embodiment, an opening angle of the control device.

This refinement may allow for an improved working with the control device, for an exemplary embodiment, whenever the control device is not directly connected mechanically to an actuator of the instrument. The resolution in the determination of the degree of opening can be chosen according to requirements. Thus, in a refinement of the disclosed subject-matter, a distinction is only made between the states of open and closed. For other exemplary embodiments, a distinction is made between the states of closed, partly opened and opened or completely opened. For yet other exemplary embodiments, the opening angle is at least approximately determined. A goniometer may be used, which determines an angle of at least one of the levers in relation to one of the other levers or the central element. The determined value of the degree of opening of the control device, for an exemplary embodiment, an angular value, may be transmitted electronically to an actuator, which may also be located at a distant location.

Furthermore, a non-surgical instrument with a manual control device for actuation by hand is also presented, wherein an actuator of the non-surgical instrument is actuated when there is an actuation of the control device. All of the explanations previously given with respect to the surgical instrument and the control device apply here.

BRIEF DESCRIPTION OF THE DRAWINGS

It is self-evident that the features mentioned above and still to be explained below can be used not only in the combination respectively specified, but also in other combinations or on their own without departing from the scope of the present disclosure.

Exemplary embodiments are represented in more detail in the drawing and are explained in more detail in the description that follows. In the drawing.

DETAILED DESCRIPTION THE INVENTION

Figure 1:
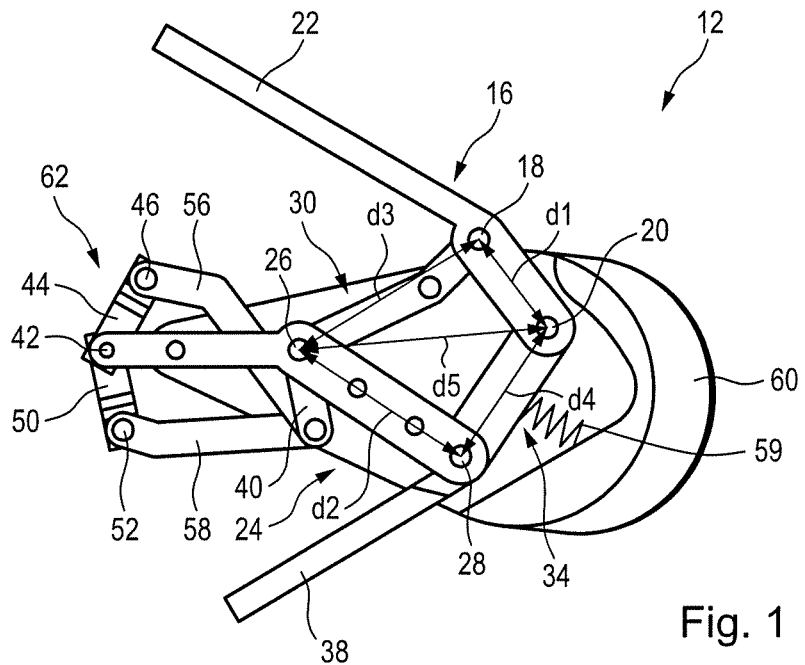
FIG. 1 shows a first embodiment of a manual control device for actuation by hand in the opened state.
Figure 12:
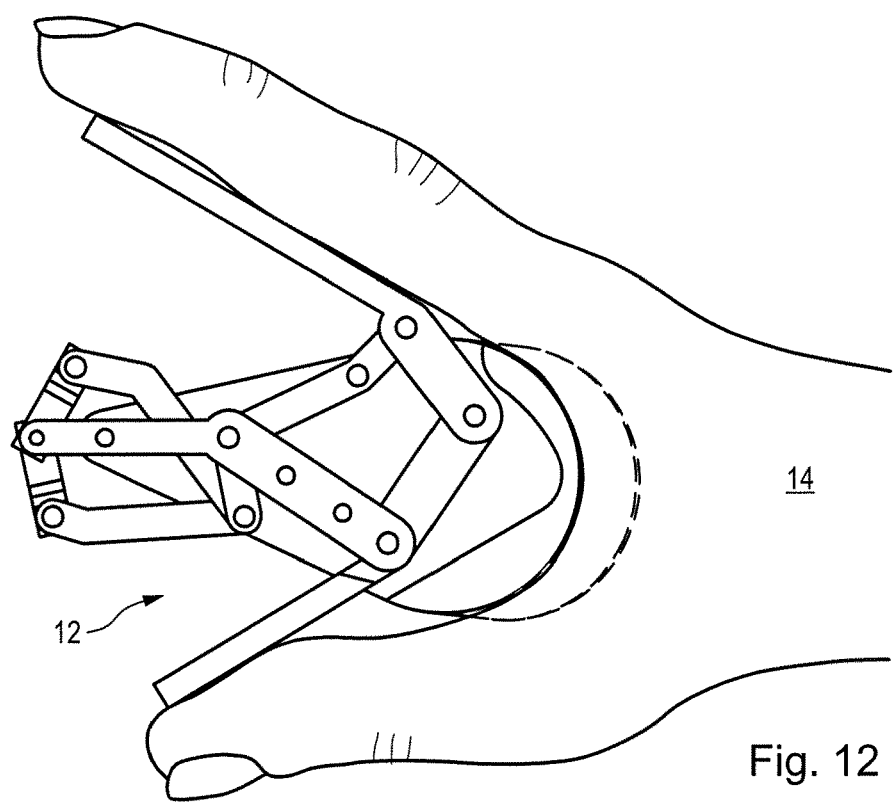
FIG. 12 shows the representation according to FIG. 1, a hand additionally being depicted.

FIG. 1 shows a manual control device 12 for actuation with a hand 14 (see FIG. 12). The control device 12 can be displaced between a closed position (see FIG. 3) and an opened position (see FIG. 1).

The control device 12 has a finger lever 16 with a first point of articulation 18 and a second point of articulation 20. The finger lever 16 also has a finger resting portion, which is formed as a continuation from the first point of articulation 18 as a first extent of the finger lever 16 between the second point of articulation 20 and the first point of articulation 18. The control device 12 also has a central element 24 with a third point of articulation 26 and a fourth point of articulation 28.

The manual control device 12 also has a connecting lever 30, which is pivotably arranged at the first point of articulation 18 and at the third point of articulation 26, so that the connecting lever 30 is pivotable in relation to the central element 24 and in relation to the finger lever 16 and that the first point of articulation 18 is displaceable along a first curved path 32 (see FIG. 4) around the third point of articulation 26.

The control device 12 also has a thumb lever 34, which is pivotably arranged at the second point of articulation 20 and at the fourth point of articulation 28, so that the thumb lever 34 is pivotable in relation to the central element 24 and in relation to the finger lever 16 and that the second point of articulation 20 is displaceable in a guided manner along a second curved path 36 around the fourth point of articulation 28.

The thumb lever 34 has a thumb resting portion 38, which is formed as a continuation from the fourth point of articulation 28 as a second extent of the thumb lever 34 between the second point of articulation 20 and the fourth point of articulation 28.

The connecting lever 30 has an actuating portion 40, which is formed as a continuation from the third point of articulation 26 as a third extent of the connecting lever 30 between the first point of articulation 18 and the third point of articulation 26.

The central element 24 has a fifth point of articulation 42. The control device 12 also has a first control element 44, which has a sixth point of articulation 46 and is pivotably arranged at the fifth point of articulation 42 and at the sixth point of articulation 46. The first control element 44 is coupled to the connecting lever 30, so that the first control element 44 is pivotable in relation to the central element 24 and that the sixth point of articulation 42 is displaceable in a guided manner along a third curved path 48 (see FIG. 4) around the fifth point of articulation 42.

The control device 12 also has a second control element 50. Here, this second control element 50 is pivotably arranged about the fifth point of articulation 42, but may also be pivotably arranged at a seventh point of articulation (not shown) that is different from the fifth point of articulation 42. The second control element 50 has an eighth point of articulation 52 and is also pivotably arranged at the eighth point of articulation 52. The second control element 50 is coupled to the connecting lever 30, so that the second control element 50 is pivotable in relation to the central element 24 and that the eighth point of articulation 52 is displaceable in a guided manner along a fourth curved path 54 (see FIG. 4) around the fifth point of articulation 42.

The connecting lever 30 and the first control element 44 are coupled by a first articulated connection, here by a first intermediate lever 56. The connecting lever 30 and the second control element 50 are coupled by a second articulated connection, here by a second intermediate lever 58.

The first point of articulation 18 and the second point of articulation 20 are spaced apart by a first distance d1. The third point of articulation 26 and the fourth point of articulation 28 are spaced apart by a second distance d2. Here, the first distance d1 is approximately 55% of the second distance d2.

The first point of articulation 18 is spaced apart from the third point of articulation 26 by a third distance d3. The second point of articulation 20 is spaced apart from the fourth point of articulation 28 by a fourth distance d4. Here, the fourth distance is approximately 75% of the third distance. Moreover, the first distance is approximately 70% of the fourth distance.

Also shown in FIG. 1 is an optional resilient element 59, with which the control device 12 can be pretensioned in the direction of an opened position. This facilitates the opening of the control device 12. The resilient element 59 may be formed by elastic materials and takes, for this exemplary embodiment, the shape like a helical spring. Other designs are also possible, however, for some exemplary embodiments, a spiral spring or a leaf spring. Here, the resilient element 59 acts on the thumb lever 34, but with appropriate positioning may also act on any other lever.

The control device 12 is formed in such a way that a fifth distance d5 between the second point of articulation 20 and the third point of articulation 26 is reduced during an opening of the control device 12. This is illustrated in the subsequent figures. In a corresponding way, the distance d5 is increased during a closing of the control device 12.

The central element 24 has a palm rest 60, on which the hand may rest ergonomically over a relatively long time, in particular over several hours, and/or may rest without suffering from fatigue. In the case of the embodiment shown here, the central element 24 also has an adapter 62 for coupling to a working portion 64 (see FIG. 5) or, if a different adapter 63 is used, to a haptic input device 66 (see FIG. 8). Here, the adapter 62 for coupling to a working portion 64 has the first control element 44 and the second control element 50.

The position of the control device 12 that is shown in FIG. 1 is referred to here as the opened state. It should be pointed out that the control device 12 can also be opened further than is shown here.

Figure 2:
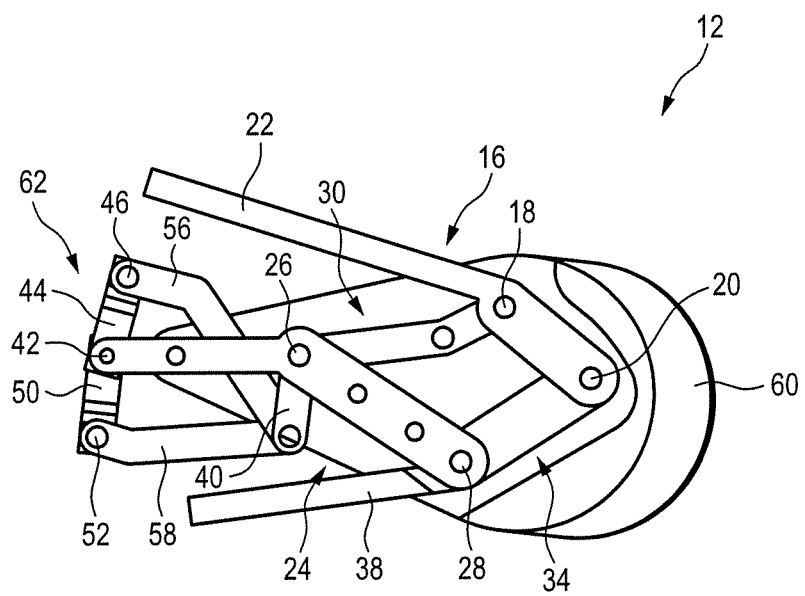
FIG. 2 shows the first embodiment according to FIG. 1 in the partly opened state.

FIG. 2 shows the control device 12 according to FIG. 1 in a partly opened state. It can be seen that the fifth distance d5 has been increased. Moreover, the position of the adapter 62, specifically the alignment of the first control element 44 and the second control element 50, has changed. If a fixed part of the working portion 64 is arranged at the fifth point of articulation 42 and at least one movable part of the working portion 64 is coupled to the first control element 44 and/or to the second control element 50, the displacement of the first and/or second control element 44, 50 can be used for an actuation of the working portion.

Figure 3:
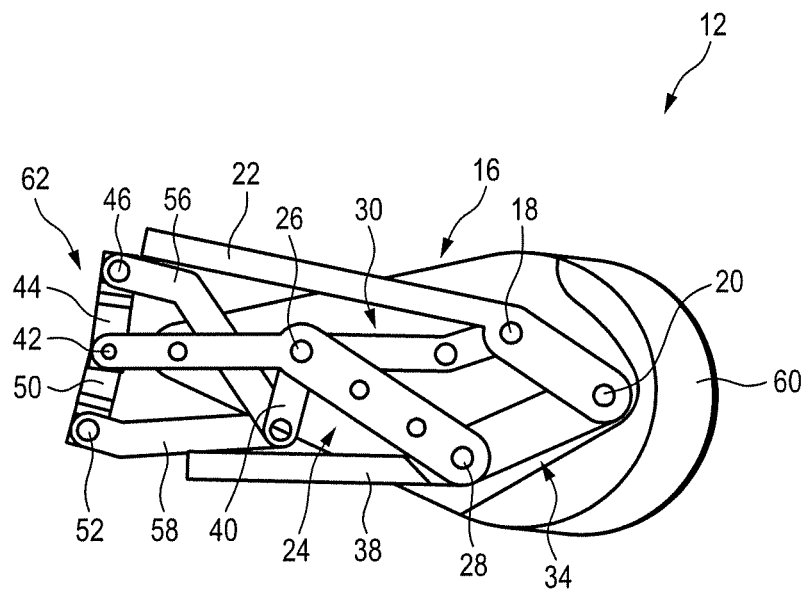
FIG. 3 shows the first embodiment according to FIG. 1 in the closed state.

FIG. 3 finally shows the first embodiment according to FIG. 1 in a closed state.

Figure 4:
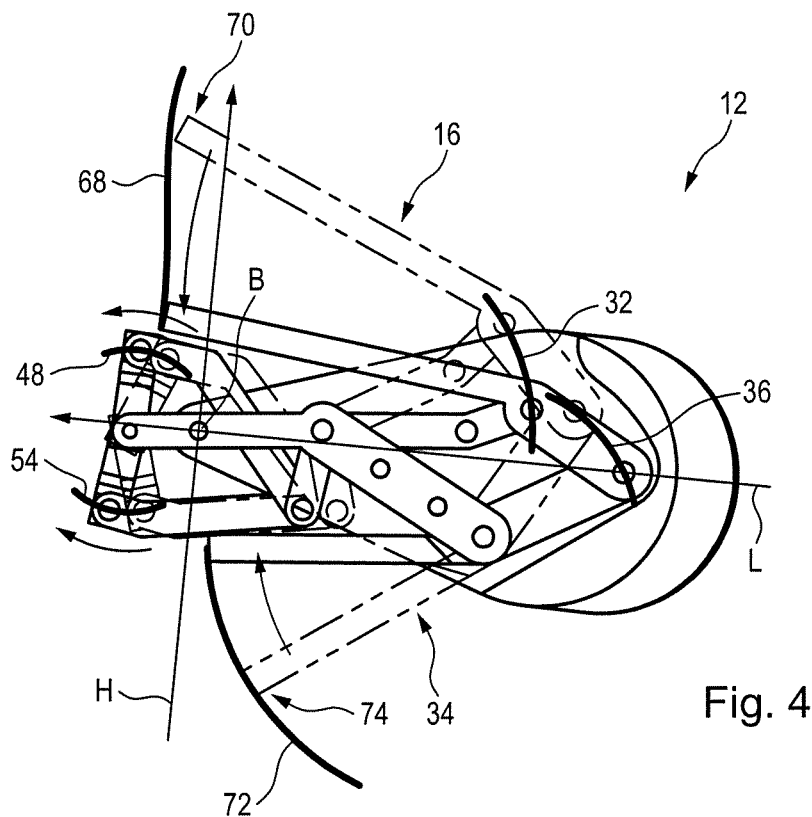
FIG. 4 shows the representation according to FIG. 3, another partly opened state having been added with a double dashed line.

FIG. 4 shows the representation according to FIG. 3 with a solid line and the representation according to FIG. 1 with a double dashed line in a superposed form. This representation allows a good appreciation of the movements of the individual parts. The previously explained paths of movement are also depicted.

Also shown here as an orientation aid are a longitudinal direction L of the control device 12 and a vertical direction H running perpendicularly thereto. A direction that runs both perpendicularly to the longitudinal direction L and perpendicularly to the vertical direction H is depicted as the width direction B and here is perpendicular to the plane of the drawing.

Additionally depicted is a finger movement path 68, which describes the movement of the first distal end 70 of the finger lever 16. Also depicted is a thumb movement path 72, which describes the movement of a second distal end 74 of the thumb lever 34. In order to ensure the overall clarity of the representation, not all of the previously introduced reference signs have been repeated in this representation. However, all of the reference signs introduced continue to apply here and hereinafter to elements that are identical or functionally the same.

Figure 5:
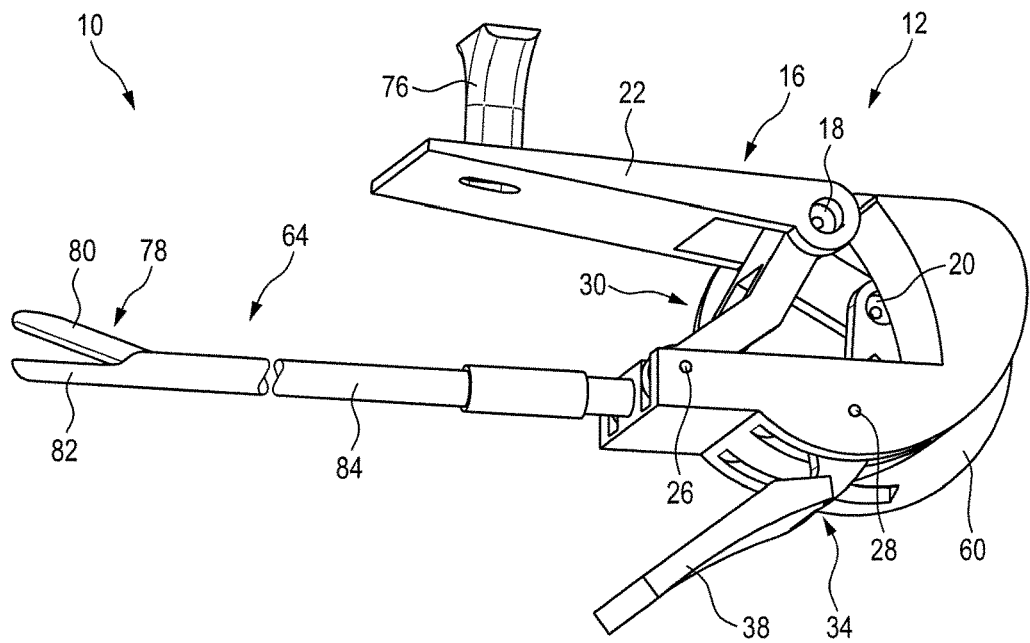
FIG. 5 shows a first embodiment of a surgical instrument with a second embodiment of a manual control device from a first perspective.

FIG. 5 shows a first embodiment of a surgical instrument 10 with a second embodiment of a control device 12. The explanations previously given in connection with the central element, the finger lever, the thumb lever and the connecting lever also apply here. In order to facilitate the upward movement during the opening of the control device 12, here a finger holder 76, also referred to as a finger pin, is arranged on the finger lever 16, to be more specific on the finger resting portion 22, it also being possible in the case of certain embodiments (not shown) for the finger holder 76 to have finger loops. The working portion 64 has an actuator 78 with a movable mouth part 80 and a fixed mouth part 82. Furthermore, the working portion 64 has a fixed part 84 and a displaceable part 86 (see FIG. 6), which is coupled to an adapter 88 (see FIG. 6). Here, the adapter 88 is detachably fixed to the thumb lever 34.

Figure 6:
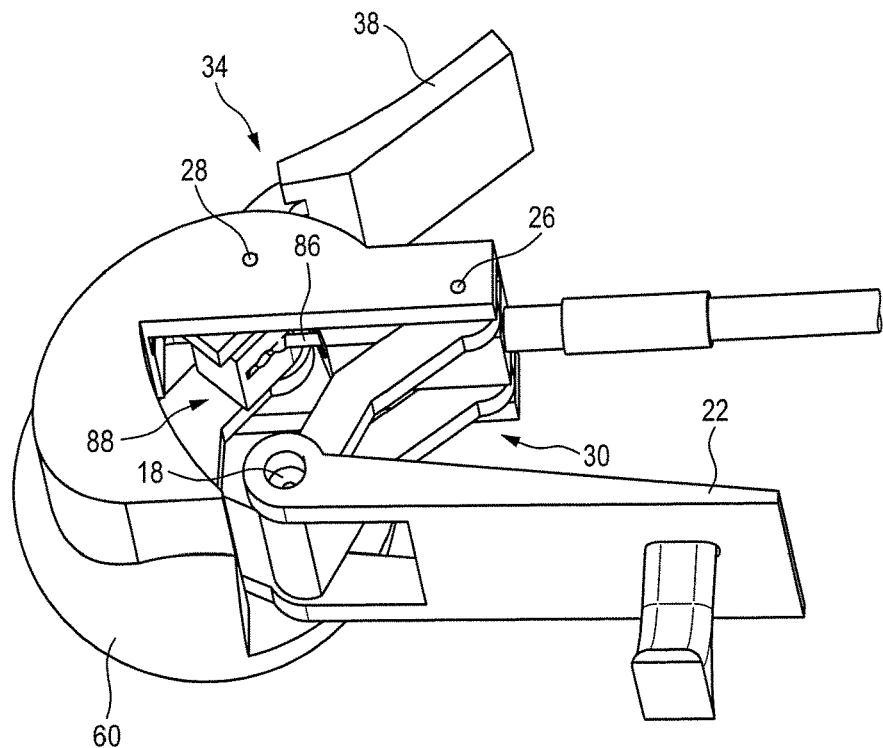
FIG. 6 shows a first embodiment of the instrument according to FIG. 5 from a second perspective.

In FIG. 6, which shows the representation according to FIG. 5 from a different perspective, it can be seen that the movement of the thumb lever can exert a positive or negative push on the movable element 86, here a push rod or a Bowden cable. The coupling by way of the movable part 86 to the movable mouthpiece 80 takes place in such a way, for example by way of a gear wheel with a toothed rack, that an opening of the control device 10 opens the actuator 78 and a closing of the control device 10 closes the actuator 78.

Figure 7:
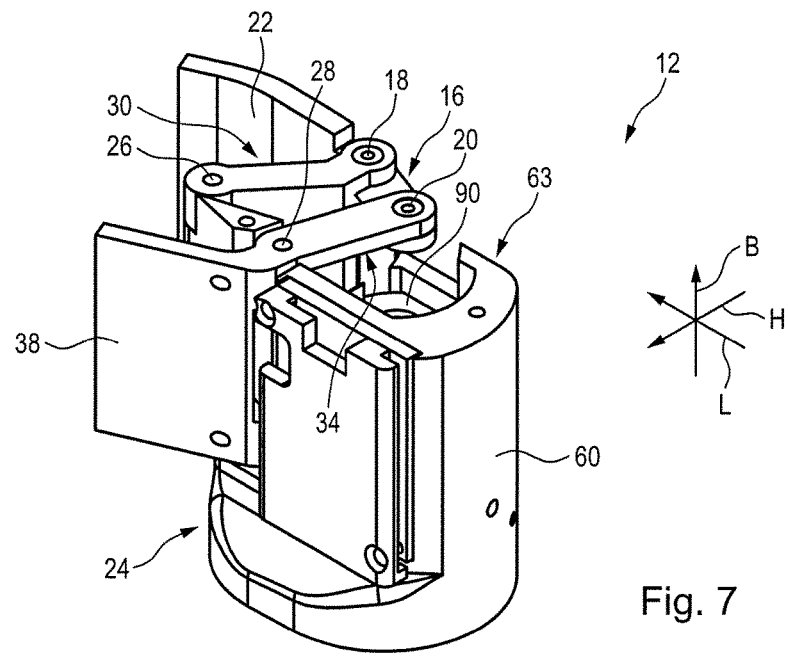
FIG. 7 shows a third embodiment of a manual control device.

FIG. 7 shows a third embodiment of a control device 12. All of the previous explanations with respect to the central element, the thumb lever, the finger lever and the connecting lever continue to apply. The third embodiment has an adapter 63 for coupling to a haptic input device 66 of the surgical instrument 10. Moreover, as still to be illustrated below, also arranged in the control device 12 is a motor 90, which here is coupled to the thumb lever 34. The use of the motor 90 allows actuation by the user to be assisted, a certain degree of opening of the control device 10 to be maintained or haptic feedback (force feedback) to be made possible. Moreover, the motor 90 may also be operated in such a way that it continuously attempts to open the control device 12 or to subject the control device 12 to a force in the direction of the opened state.

Figure 8:
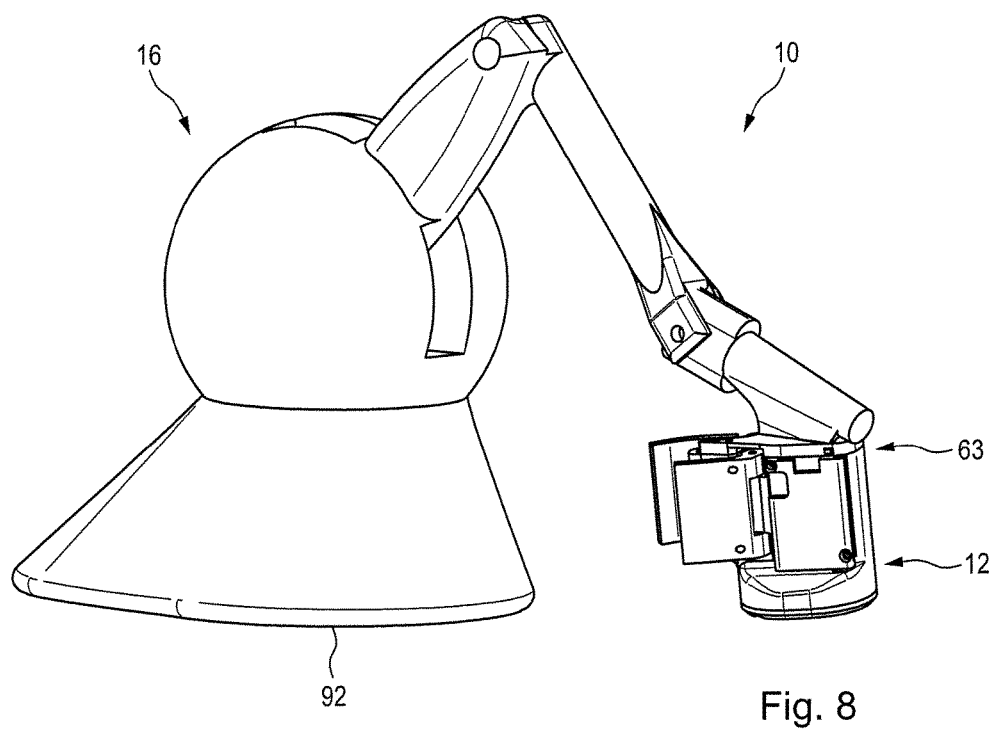
FIG. 8 shows a second embodiment of a surgical instrument with a control device according to FIG. 7, which is coupled to a haptic input device.

FIG. 8 shows a second embodiment of the surgical instrument with a working portion 91, which here is actuated on the basis of control signals of the haptic input device 66.

It can be seen here that the width of the control device 12, that is to say the extent along the width direction B, is at least 50% of the width of a human hand, or at least 75%, or at least 85% or at least 95%.

Figure 9:
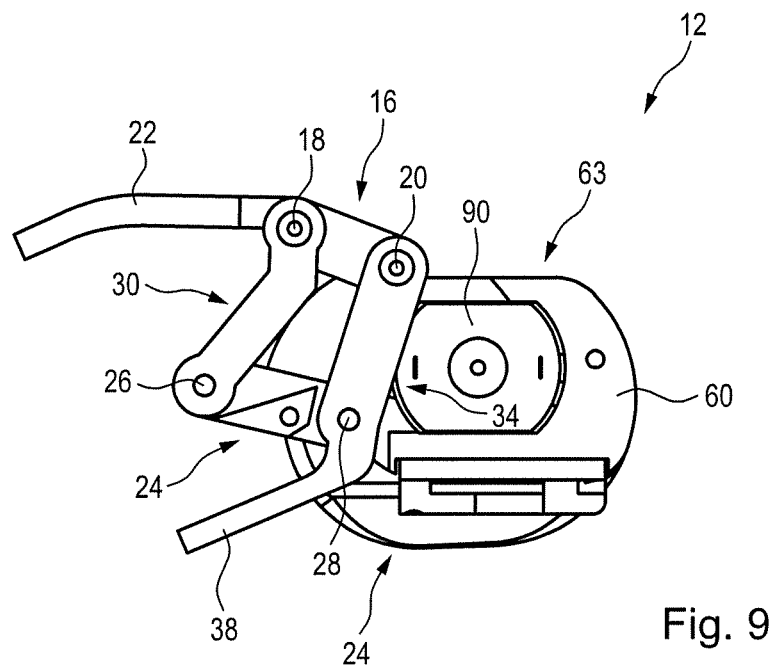
FIG. 9 shows the third embodiment of the control device according to FIG. 7 in a first side view.
Figure 10:
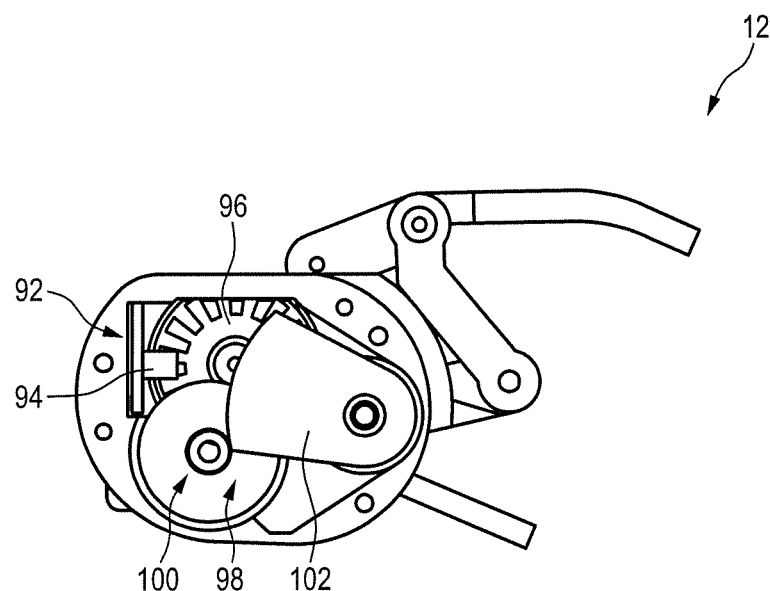
FIG. 10 shows the third embodiment of the control device according to FIG. 7 in a second side view.

FIG. 9 shows the representation according to FIG. 7 in a first side view. FIG. 10 shows the representation according to FIG. 7 in a second side view. A second measuring device 92 can be seen here, designed for determining a degree of opening of the control device 12, for an exemplary embodiment, an opening angle of the control device. For this, the measuring device 92 has a sensor 94 and a signal transmitter 96, which here is coupled to the thumb lever 34, for an exemplary embodiment, by way of a gear mechanism.

In the case of other designs, the signal transmitter 96 may also be coupled to the connecting lever 30 or to the finger lever 16. Also shown is a transmission mechanism, which transmits a torque of the motor 90 to a small wheel 100, for an exemplary embodiment, a gear wheel, which is coupled to the thumb lever 34 by way of a transmission lever 102. In this way, the motor 90 can be coupled to the thumb lever 34 with a high reduction ratio.

Figure 11:
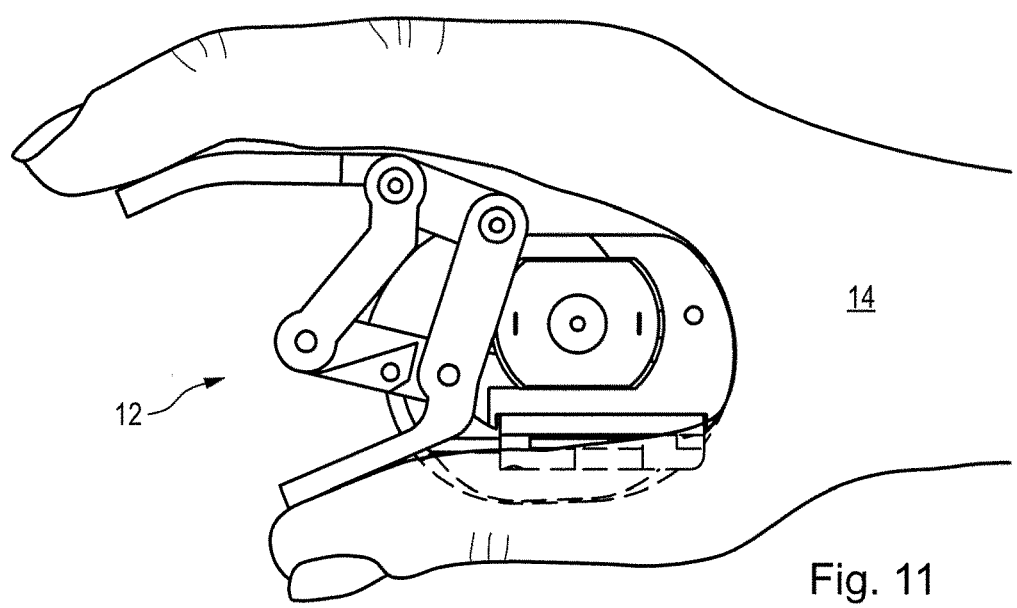
FIG. 11 shows the representation according to FIG. 9, a hand additionally being depicted.

FIG. 11 shows the third embodiment of the control device 12 with a placed-on hand 14.

FIG. 12 shows the first embodiment of the control device 12 with a placed-on hand 14.

Figure 13:
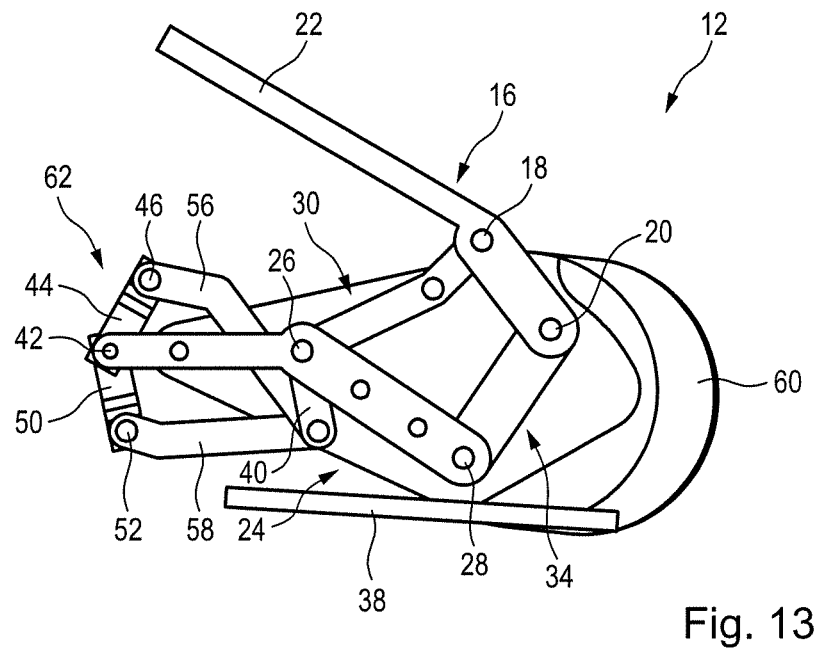
FIG. 13 shows a fourth embodiment of a manual control device.

FIG. 13 shows a fourth embodiment of a manual control device 12 with a thumb resting portion 38, which is not formed as a continuation of the thumb lever. Here, the thumb resting portion 38 is fixed in relation to the central element 24. During the opening and closing of the control device 12, the user only moves his or her fingers. There are also exemplary embodiments in which there is no thumb resting portion at all.

Figure 14:
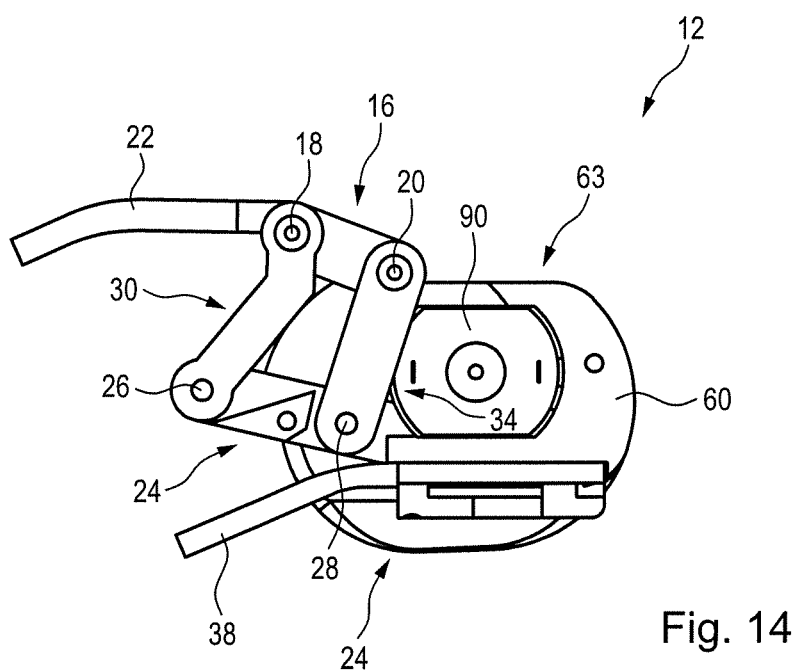
FIG. 14 shows a fifth embodiment of a manual control device.

FIG. 14 shows a fifth embodiment of a manual control device 12, in which the thumb resting portion 38 is likewise fixed in relation to the central element 24.

The design of the palm rest 60 or the gripping piece of the grip of the surgical instrument 10 is important for ergonomic gripping. Three of the exemplary embodiments that may be regarded as having improved ergonomics are described below.

Figure 15:
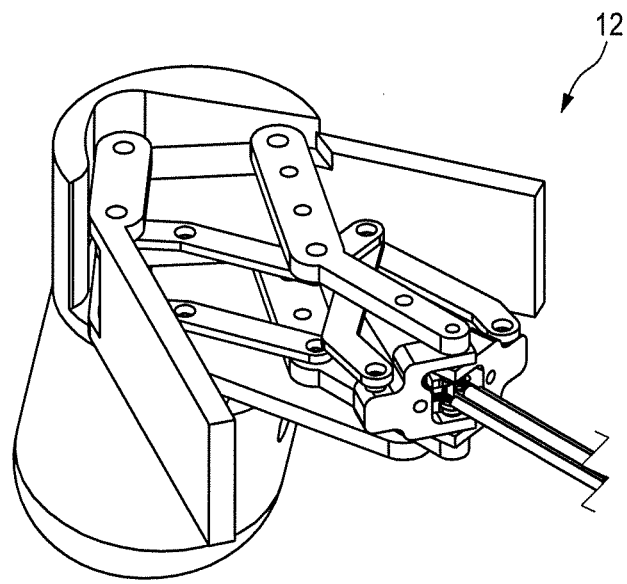
FIG. 15 shows the first embodiment of a manual control device with a pistol-like grip in a perspective view.
Figure 16:
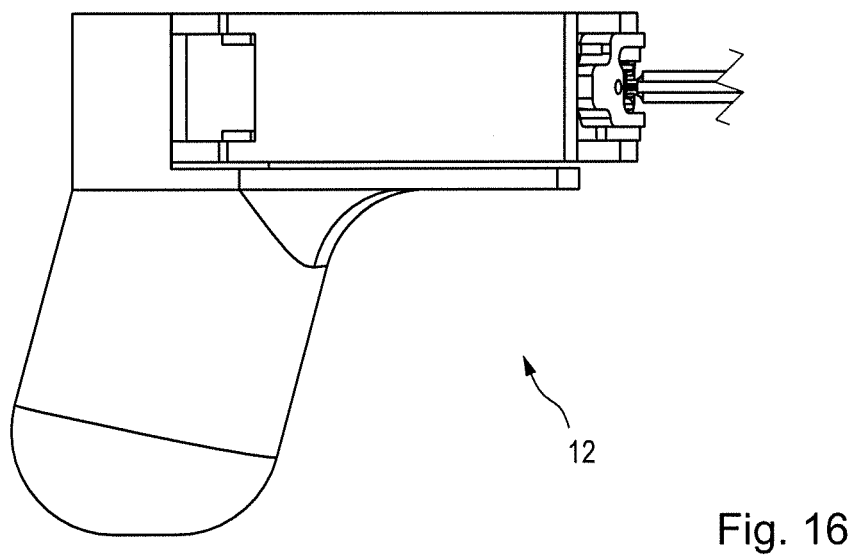
FIG. 16 shows the first embodiment of a manual control device with a pistol-like grip in a plan view.

FIGS. 15 and 16 show the first embodiment of a manual control device 12 with a pistol-like grip in a perspective view and in a plan view, respectively. All of the reference signs continue to apply in the same way as they have already been introduced and are not repeated here.

Figure 17:
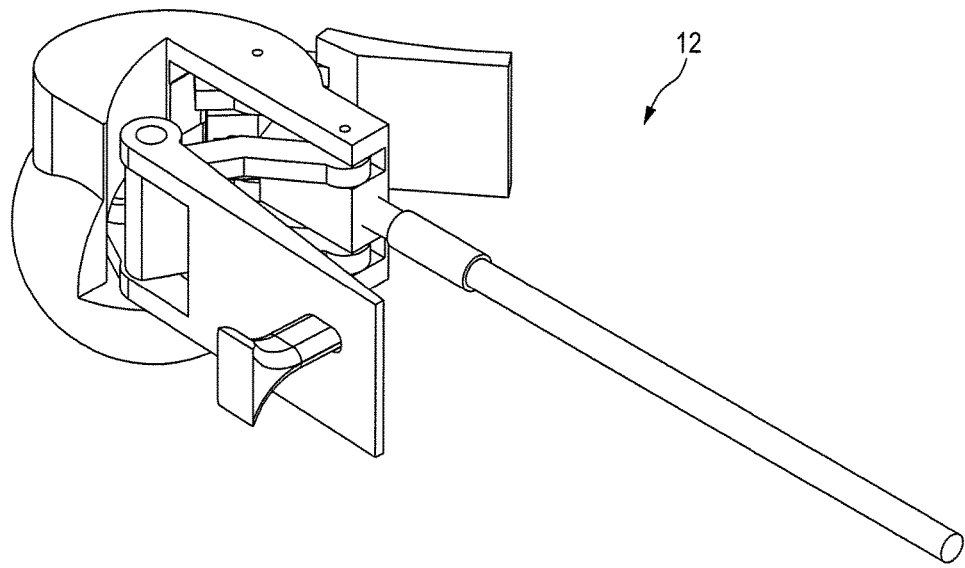
FIG. 17 shows the second embodiment of a manual control device with a ball-like grip in a perspective view.
Figure 18:
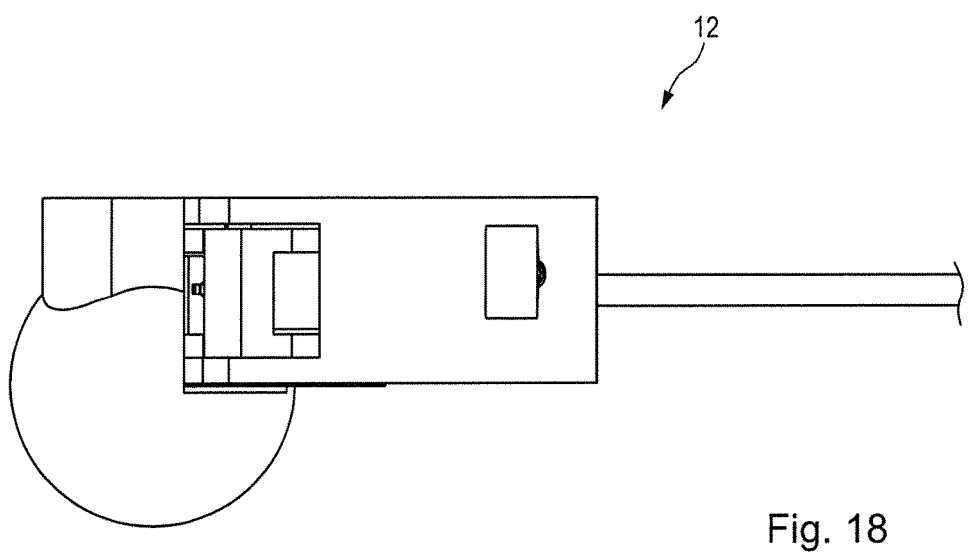
FIG. 18 shows the second embodiment of a manual control device with a ball-like grip in a plan view.

FIGS. 17 and 18 show the second embodiment of a manual control device 12 with a ball-like grip in a perspective view and in a plan view, respectively. All of the reference signs continue to apply in the same way as they have already been introduced and are not repeated here.

Figure 19:
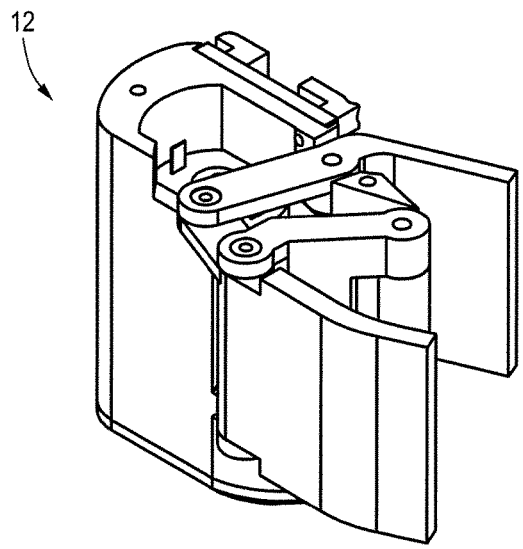
FIG. 19 shows the third embodiment of a manual control device with a stub-like grip in a first perspective view.
Figure 20:
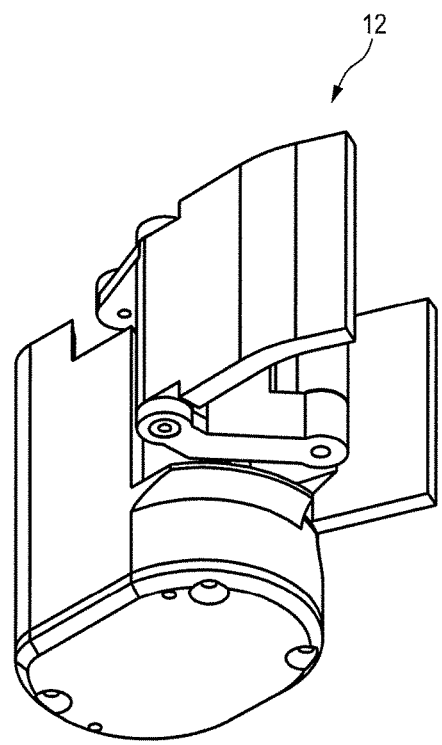
FIG. 20 shows the third embodiment of a manual control device with a stub-like grip in a second perspective view.
Figure 21:
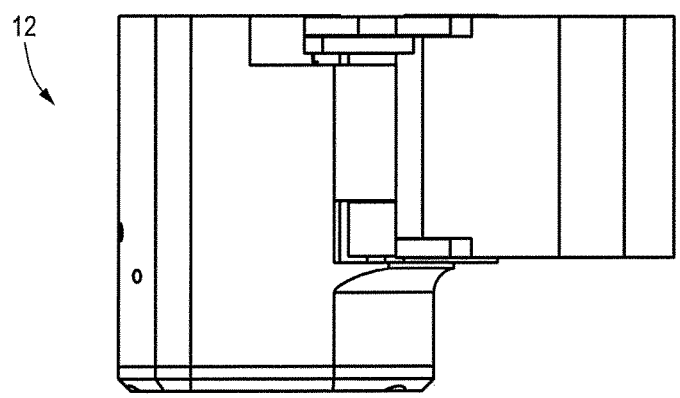
FIG. 21 shows the third embodiment of a manual control device with a stub-like grip in a plan view.

FIGS. 19, 20 and 21 show the first embodiment of a manual control device 12 with a stub-like grip in a first and a second perspective view and in a plan view, respectively. All of the reference signs continue to apply in the same way as they have already been introduced and are not repeated here.

The invention claimed is:

1. A surgical instrument with a manual control device for actuation with a hand, wherein the control device can be displaced between a closed position and an opened position and the control device comprises:
   a finger lever with a first point of articulation and a second point of articulation, wherein the finger lever has a finger resting portion, which is formed as a continuation from the first point of articulation as a first extent of the finger lever between the second point of articulation and the first point of articulation,
   a central element with a third point of articulation and a fourth point of articulation,
   a connecting lever, which is pivotably arranged at the first point of articulation and at the third point of articulation, so that the connecting lever is pivotable in relation to the central element and in relation to the finger lever and that the first point of articulation is displaceable in a guided manner along a first curved path around the third point of articulation,
   a thumb lever, which is pivotably arranged at the second point of articulation and at the fourth point of articulation, so that the thumb lever is pivotable in relation to the central element and in relation to the finger lever and that the second point of articulation is displaceable in a guided manner along a second curved path around the fourth point of articulation.

2. The surgical instrument of claim 1, wherein the thumb lever has a thumb resting portion, which is formed as a continuation from the fourth point of articulation as a second extent of the thumb lever between the second point of articulation and the fourth point of articulation.

3. The surgical instrument of claim 1, wherein the connecting lever has an actuating portion, which is formed as a continuation from the third point of articulation as a third extent of the connecting lever between the first point of articulation and the third point of articulation.

4. The surgical instrument of claim 1, wherein the central element has a fifth point of articulation and the control device has a first control element, which has a sixth point of articulation, is pivotably arranged at the fifth point of articulation and at the sixth point of articulation and is coupled to the connecting lever, so that the first control element is pivotable in relation to the central element and that the sixth point of articulation is displaceable in a guided manner along a third curved path around the fifth point of articulation.

5. The surgical instrument of claim 1, wherein the central element has a seventh point of articulation and the control device has a second control element, which has an eighth point of articulation, is pivotably arranged at the seventh point of articulation and at the eighth point of articulation and is coupled to the connecting lever, so that the second control element is pivotable in relation to the central element and that the eighth point of articulation is displaceable in a guided manner along a fourth curved path around the seventh point of articulation.

6. The surgical instrument of claim 4, wherein the connecting lever and the first control element are coupled by a first articulated connection.

7. The surgical instrument of claim 4, wherein the connecting lever and the first control element are coupled by a first intermediate lever.

8. The surgical instrument of claim 5, wherein the connecting lever and the second control element are coupled by a second articulated connection.

9. The surgical instrument of claim 5, wherein the connecting lever and the second control element are coupled by a second intermediate lever.

10. The surgical instrument of claim 1, wherein the first point of articulation is spaced apart from the second point of articulation by a first distance, the third point of articulation is spaced apart from the fourth point of articulation by a second distance and the first distance is between 25% and 125% of the second distance.

11. The surgical instrument of claim 1, wherein the first point of articulation is spaced apart from the third point of articulation by a third distance, the second point of articulation is spaced apart from the fourth point of articulation by a fourth distance and the fourth distance is between 35% and 150% of the third distance.

12. The surgical instrument of claim 1, wherein the first point of articulation is spaced apart from the second point of articulation by a first distance, the second point of articulation is spaced apart from the fourth point of articulation by a fourth distance and the first distance is between 40% and 150% of the third distance.

13. The surgical instrument of claim 1, further comprising a push rod, which is coupled in an articulated manner to at least one of the finger lever, the thumb lever and the connecting lever.

14. The surgical instrument of claim 1, wherein the control device is formed in such a way that a fifth distance between the second point of articulation and the third point of articulation is reduced during an opening of the control device.

15. The surgical instrument of claim 1, wherein the central element has at least one of a palm rest, an adapter for a coupling to a working portion of the surgical instrument and an adapter for a coupling to a haptic input device of the surgical instrument.

16. The surgical instrument of claim 1, further comprising a motor, which interacts with at least one of the finger lever, the thumb lever and the connecting lever, in order to provide at least one of haptic feedback and motorized assistance.

17. The surgical instrument of claim 1, further comprising a measuring device, which is designed for determining a degree of opening of the control device.

18. The surgical instrument of claim 1, further comprising a measuring device, which is designed for determining an opening angle of the control device.

* * * * *